United States Patent [19]

Melas

[11] Patent Number: 4,740,606

[45] Date of Patent: Apr. 26, 1988

[54] GALLIUM HYDRIDE/TRIALKYLAMINE ADDUCTS, AND THEIR USE IN DEPOSITION OF III-V COMPOUND FILMS

[75] Inventor: Andreas A. Melas, Burlington, Mass.

[73] Assignee: Morton Thiokol, Inc., Chicago, Ill.

[21] Appl. No.: 680,760

[22] Filed: Jul. 1, 1986

[51] Int. Cl.$^4$ .............................................. C07F 5/00
[52] U.S. Cl. ....................................................... 556/1
[58] Field of Search ........................................... 556/1

[56] References Cited

U.S. PATENT DOCUMENTS 3,318,931  5/1967  Dötzer et al. ............................ 556/1
3,607,257  9/1971  Johnson .................................. 556/1

OTHER PUBLICATIONS

Chemical Abstracts vol. 79: 77865z (1973).
Chemical Abstracts vol. 77: 114477f (1972).
Chemical Abstracts vol. 88: 82962u (1978).
Matloubian, et al., "MOCVD Epitaxial Growth of Single Crystal GaN, AlN, and AL$_x$Ga$_{1-x}$N," *Journal of Electronic Materials*, vol. 14, No. 5, pp. 633–644, 1985.
Shirk, et al. "Lithium Tetrahydridogallate," *Inorganic Syntheses*, vol. 17, pp. 45–47 (1980).
Shiver, et al., "Trihydrido(Trimethylamine)Gallium", *Inorganic Synthesis*, vol. 17, pp. 42–44, 1980.

*Primary Examiner*—Paul F. Shaver
*Attorney, Agent, or Firm*—George Wheeler; Gerald K. White

[57] ABSTRACT

Adduct of the formula:

$$H_3GaNR_3$$

wherein each R is independently selected from lower alkyl having from 2 to about 4 carbon atoms, and a process for depositing gallium nitride, gallium arsenide, or gallium phosphide films, using the above adduct as a source of nitride (for the nitride film) and gallium. Arsenic and phosphorus compounds are also added for depositing gallium compounds of those elements. The process can also be performed using the analogous trimethylamine adduct.

2 Claims, No Drawings

GALLIUM HYDRIDE/TRIALKYLAMINE ADDUCTS, AND THEIR USE IN DEPOSITION OF III-V COMPOUND FILMS

TECHNICAL FIELD

The present invention relates to methods of depositing III-V films, particularly wherein the Group III element is gallium and the group V element is selected from arsenic, phosphorus, and nitrogen.

The present invention relates further to novel adducts of gallane ($GaH_3$) with lower alkyl amines.

BACKGROUND ART

The 1:1 adduct of gallane (gallium hydride) and trimethylamine is known. Its preparation is taught in Shriver, et al., "Trihydrido(trimethylamine)gallium", *Inorganic Syntheses*, Vol. 17, pages 42-44 (1980). Preparation of the lithium gallium hydride starting material recited in the foregoing article is taught in Skirk, et al., "Lithium tetrahydridogallate," *Inorganic Syntheses*, Vol. 17, pages 45-47 (1980). No use for the adduct is reported in these articles. The adduct has a melting point of 69° C., and is sublimable. Consequently, it is not an ideal candidate for use in metal organic chemical vapor deposition (MOCVD), for which compounds in liquid form at or near room temperature are desired. Also, higher alkyl compounds analogous to this adduct are not known.

Gallium arsenide, gallium phosphide, and related compounds have previously been produced by introducing trimethylgallium and arsine ($AsH_3$) or phosphine ($PH_3$) to a substrate in a heated deposition chamber of MOCVD (metal organic chemical vapor deposition) apparatus. At the deposition temperature, the source compounds decompose and react at the surface of the substrate to form a gallium arsenide or gallium phosphide film.

A similar reaction in which the arsine or phosphine of the prior art are replaced by alkyl arsenic hydride or alkyl phosphorus hydride is described in U.S. Ser. No. 828,467, filed Feb. 10, 1986 and owned in common with the present application. (That application is hereby incorporated herein by reference.)

One disadvantage of the prior art technique in which arsine or phosphine are used as the Group V element sources is that these source compounds are gaseous and extremely toxic; consequently they are extremely expensive and potentially hazardous to handle. Use of trialkyl arsine and trialkyl phosphine in conjunction with trialkyl gallium for forming III-V films has the disadvantage of not providing any source of monatomic hydrogen. Monatomic hydrogen can combine with the alkyl radicals released during decomposition to form gaseous carbon reaction products such as methane, ethane, ethylene, and the like, which can be transported out of the deposition chamber. If monatomic hydrogen is not present, the alkyl radicals released during decomposition of the source compounds contribute to carbon contamination of the desired film.

Matloubian, et al., "MOCVD Epitaxial Growth of Single Crystal GaN, AlN, and $AL_xGa_{1-x}N$," *Journal of Electronic Materials*, Vol. 14, No. 5, pp 633-644 (1985) teaches conditions under which gallium nitride films and other films of III-V compounds have been grown using MOCVD.

SUMMARY OF THE INVENTION

A first aspect of the present invention is an adduct of the formula:

wherein each R is independently selected from alkyl groups having from 2 to about 4 carbon atoms. The upper limit of this range is not critical.

A second aspect of the invention is a method for depositing a gallium nitride film on a substrate, comprising the steps of selecting as a source compound an adduct having the previously stated formula (except that the alkyl group can have from 1 to about 4 carbon atoms in this aspect of the invention), conveying the source compound to a deposition chamber containing a substrate to receive a deposit, and decomposing the source compound in the deposition chamber. As a result, a gallium nitride film is deposited on the substrate. At least some, and preferably all of the alkyl radicals released by decomposition of the trialkylamine portion of the adduct react with some or all of the monatomic hydrogen formed by decomposition of the gallium hydride portion of the adduct, forming gaseous hydrocarbon waste products which can be removed from the deposition chamber easily. The adducts in which R is a moiety having from 2-4 carbon atoms are preferred because they are liquids and thus can be conveniently provided by passing a carrier gas through a bubbler containing the source compound. The trimethylamine adduct can also be provided in this fashion from a bubbler maintained at a temperature exceeding about 70° C., but requires that the vapor transmission lines must be heated to prevent condensation of the adduct.

A further aspect of the invention is the use of the gallium source compounds just described in combination with a Group V element source compound, for example an arsenic compound or a phosphorus compound, to deposit a III-V compound on a substrate. This process is analogous to the previous process, and also to known processes in which III-V compound films are formed, except that the gallium adduct replaces trialkylgallium compounds previously used as the gallium source compound.

One advantage of the present gallium adducts as source compounds is that the gallium-to-hydrogen bond can readily be broken in the deposition chamber at an elevated temperature, providing monatomic hydrogen which is free to react with alkyl radicals left by the decomposition of alkyl-substituted source compounds. A second advantage of the present gallium adducts as source compounds for formation of gallium nitride films is that the gallium-to-nitrogen bond is already formed; this encourages the ultimate formation of a gallium nitride film. A third advantage of the present gallium source compounds is that their products of decomposition at room temperature are gallane and a trialkylamine, each of which is nontoxic compared to other source compounds.

DETAILED DESCRIPTION OF THE INVENTION

The adducts of gallium hydride and trialkylamines contemplated herein are 1:1 adducts having the following structural formula:

in which the gallium and nitrogen atoms are directly bonded, the hydrogen moieties are bonded to gallium, and the alkyl moieties are bonded to nitrogen. For the novel compounds contemplated here, R is alkyl of from 2 to about 4 carbon atoms, the upper limit of carbon atoms not being critical. Specific adducts contemplated herein are the following:

$H_3GaN(C_2H_5)_3$ $H_3GaN(CH_2CH_2CH_3)_3$ $H_3GaN[C(CH_3)_3]_3$ $H_3GaN(C_2H_5)_2(CH_2CH_2CH_3)$

As indicated above, both homosubstituted and heterosubstituted compounds are contemplated herein. Also, the alkyl groups can be straight or branched alkyl groups. The alkyl groups are selected from ethyl, propyl, isopropyl, any of the 4 butyl isomers, etc.

The present compounds are made according to the procedure in Example 1. The different substituents in homo- or heterosubstituted adducts are provided by selecting the corresponding amine hydrochloride starting material.

One particular adduct preferred herein is the adduct in which each R is ethyl. This adduct is a liquid at room temperature, and thus well suited to the requirements of metal organic chemical vapor deposition.

The gallium hydride/trialkylamine adducts described above or trimethylamine adducts of the prior art can be used to deposit a gallium nitride film on a substrate. The chosen source compound is selected and placed in a bubbler having an outlet connected to a deposition chamber. The source compound is maintained as a liquid in the bubbler, and can be transported into the deposition chamber by passing a carrier gas through the bubbler. The carrier gas is introduced below the surface of the source compound, and bubbles up through the source compound to the headspace above it, entraining vapor of the source compound in the carrier gas. The entrained vapor then passes into the deposition chamber. The preferred carrier gas contains nitrogen to encourage the formation of additional nitride, and optionally hydrogen, which tends to reduce and remove any oxygen in the system. The preferred carrier gas is a mixture of about 90% nitrogen and 10% hydrogen. Inert gases may also be incorporated in the carrier gas.

The deposition chamber is a heated vessel within which is disposed at least one, and preferably many substrates. The deposition chamber has an outlet which is typically connected to a vacuum pump in order to draw by-products out of the chamber and to provide a reduced pressure where that is appropriate. (MOCVD can be conducted at atmospheric pressure or at a reduced pressure.) The deposition chamber is maintained at a temperature sufficiently high to induce decomposition of the source compound. The typical deposition chamber temperature is from about 300° C. to about 1000° C., the exact temperature selected being optimized to provide efficient deposition. Optionally, the temperature of the deposition chamber as a whole can be reduced if the substrate is maintained at an elevated temperature, or if other energy such as radio frequency energy is generated by an RF source.

The substrate for deposition can be silicon, gallium arsenide, indium phosphide, or other substrates which are lattice-matched to the crystal structure of gallium nitride.

Deposition is continued as long as desired to produce a film having the desired properties. Typically, the film thickness will be from several hundred to several thousand Angstroms or more when deposition is concluded.

The method for depositing a III-V compound other than gallium nitride is similar to the above, except that a source of the desired Group V element must also be provided. While arsine or phosphine can be used as a Group V source compound, to avoid excessive toxicity it is desirable to use the partially hydrocarbon-substituted phosphine and arsine analogs disclosed in the previously incorporated commonly owned patent application. These compounds are much less toxic than arsine or phosphine, and many of them are in a liquid form which is more easily metered than a material which is gaseous or solid at the temperature at which it is supplied. Typically, a second bubbler is provided to supply the second source compound to the same deposition chamber.

One utility contemplated for the present adducts is formation of nitrogen-doped gallium phosphide or nitrogen-doped aluminum gallium phosphide films. Such films are used in yellow light emitting diodes; the degree of nitrogen doping affects the color of the emitted light. Since the present gallium adduct is a source of nitrogen bonded to gallium, simultaneous introduction of the present adducts, a phosphorus source compound such as a mono- or dialkylphosphine, and optionally an aluminum source compound into a deposition chamber will cause displacement of most of the nitrogen atoms of the adduct by phosphorus (and optionally aluminum) atoms. By adjusting the reaction conditions, the amount of doping is regulated. This process eliminates one step of the prior two-step process in which gallium phosphide is formed, then exposed to a nitrogen compound to dope it.

EXAMPLE 1

In this Example, $GaH_3N(CH_2CH_3)_3$ was prepared. The first stage reaction was as follows:

$4LiH + GaCl_3 \rightarrow LiGaH_4 + 3LiCl$

A one liter, three-neck flask was connected to a source of nitrogen, an addition funnel, and a flexible tube. A 25 gram ampoule of gallium chloride was opened and inverted in one neck of the flask. The ampoule was heated with a heat gun to melt the gallium chloride, which dripped into the flask. The flask was cooled to −78° C., then about 500 ml. of diethyl ether were added. The flask contents were warmed enough (by removing the cold bath temporarily) to dissolve the gallium trichloride (while stirring the mixture with a magnetic stirrer). When the contents were dissolved, the flask was returned to −78° C. 20 grams (2.53 mols.) of lithium hydride powder were added by pouring it from a small flask connected to the reaction pot with the flexible tube, while stirring the reaction mixture. After all the lithium hydride had been added, the dry ice bath was removed and the reaction mixture allowed to slowly warm to room temperature. The mixture was stirred overnight at room temperature, then filtered to remove lithium chloride and excess lithium hydride. The lithium gallium hydride was not isolated.

The second stage reaction was as follows:

$$LiGaH_4 + N(CH_2CH_3)_3/HCl \rightarrow H_3GaN(CH_2CH_3)_3 + LiCl + H_2$$

The lithium gallium hydride solution from the previous reaction was placed in a one liter flask. A supply of triethylamine hydrochloride was washed with diethyl ether in a flask, then the flask was evacuated and held under vacuum for about an hour to remove excess ether. About 19 grams (0.14 mols.) of the washed triethylamine hydrochloride were added slowly with stirring to the lithium gallium hydride solution at $-78°$ C. (The triethylamine hydrochloride was added from a side flask through a flexible tube connected to the reaction flask.) They reacted, forming hydrogen and lithium chloride. The reaction mixture was allowed to warm slowly to room temperature, then stirred overnight with a magnetic stirrer. The reaction mixture was filtered and the diethyl ether removed under vacuum. The product was a yellow liquid. The product is distilled by heating it very gently to slightly above room temperature. (The material has been found to decompose when placed in an 80° C. bath.) The end product is a colorless liquid at room temperature.

I claim:

1. An adduct of the formula:

$$H_3GaNR_3$$

wherein each R is independently selected from alkyl having from 2 to about 4 carbon atoms.

2. The adduct of claim 1, wherein each R is ethyl.

* * * * *

UNITED STATES PATENT AND TRADEMARK OFFICE
CERTIFICATE OF CORRECTION

PATENT NO. : 4,740,606

DATED : April 26, 1988

INVENTOR(S) : Melas

It is certified that error appears in the above-identified patent and that said Letters Patent is hereby corrected as shown below:

On the Title page, Column 1, Appln. No.: "680,760" should be --880,760--.

Signed and Sealed this

Thirteenth Day of February, 1990

Attest:

JEFFREY M. SAMUELS

Attesting Officer     Acting Commissioner of Patents and Trademarks